United States Patent
Smith et al.

(10) Patent No.: US 9,949,647 B2
(45) Date of Patent: Apr. 24, 2018

(54) SENSOR AND GUIDE WIRE ASSEMBLY

(75) Inventors: Leif Smith, Uppsala (SE); Ola Hammarström, Lerdala (SE); Per Egnelöv, Phuket (TH); Dan Åkerfeldt, Uppsala (SE)

(73) Assignee: ST. JUDE MEDICAL COORDINATION CENTER BVBA, Zaventem (BE)

( * ) Notice: Subject to any disclaimer, the term of this patent is extended or adjusted under 35 U.S.C. 154(b) by 1128 days.

(21) Appl. No.: 11/628,251

(22) PCT Filed: Jun. 1, 2005

(86) PCT No.: PCT/SE2005/000826
§ 371 (c)(1),
(2), (4) Date: Dec. 1, 2006

(87) PCT Pub. No.: WO2005/118047
PCT Pub. Date: Dec. 15, 2005

(65) Prior Publication Data
US 2009/0118643 A1 May 7, 2009

Related U.S. Application Data

(60) Provisional application No. 60/576,602, filed on Jun. 4, 2004.

(30) Foreign Application Priority Data

Jun. 4, 2004 (SE) .................................... 0401431

(51) Int. Cl.
*A61B 5/0215* (2006.01)
*A61B 5/00* (2006.01)
(Continued)

(52) U.S. Cl.
CPC .......... *A61B 5/0215* (2013.01); *A61B 5/6851* (2013.01); *A61M 25/09* (2013.01);
(Continued)

(58) Field of Classification Search
CPC .......... A61M 25/09; A61M 2025/0002; A61M 2025/09083; A61M 2025/09175;
(Continued)

(56) References Cited

U.S. PATENT DOCUMENTS 5,313,957 A * 5/1994 Little .......................... 600/561
RE35,648 E  11/1997 Tenerz et al.
(Continued)

FOREIGN PATENT DOCUMENTS

EP  0 925 803 A2  6/1999
JP  2001-286447 A  10/2001
WO  WO 03/030982 A2  4/2003

*Primary Examiner* — Adam J Eiseman
(74) *Attorney, Agent, or Firm* — Foley & Lardner LLP

(57) ABSTRACT

The invention relates to a sensor and guide wire assembly (21) for intravascular measurements of physiological variables in a living body, comprising a core wire (22), a first coil (23), a jacket (24), and a second coil (25). The jacket (24) comprises a first end portion (24a), which is crimped onto the core wire (22) and over which a portion of the first coil (23) is threaded, and a second end portion (24b), which is crimped onto the core wire (22) and over which a portion of the second coil (25) is threaded.

13 Claims, 2 Drawing Sheets

(51) Int. Cl.
*A61M 25/09* (2006.01)
*A61M 25/00* (2006.01)

(52) U.S. Cl.
CPC .............. *A61M 2025/0002* (2013.01); *A61M 2025/09083* (2013.01); *A61M 2025/09175* (2013.01)

(58) Field of Classification Search
CPC .............. A61B 5/0215; A61B 5/02152; A61B 5/02154; A61B 5/02158; A61B 5/6851
USPC ................................ 600/485, 486, 488, 585
See application file for complete search history.

(56) References Cited

U.S. PATENT DOCUMENTS

| | | | |
|---|---|---|---|
| 5,715,827 A | | 2/1998 | Corl et al. |
| 6,167,763 B1 | * | 1/2001 | Tenerz et al. .................. 73/756 |
| 6,190,332 B1 | * | 2/2001 | Muni et al. .................. 600/585 |
| 6,336,906 B1 | * | 1/2002 | Hammarstrom et al. .... 600/585 |
| 6,409,677 B1 | * | 6/2002 | Tulkki .......................... 600/561 |
| 6,615,667 B2 | * | 9/2003 | Smith ............................ 73/719 |
| 2003/0028128 A1 | * | 2/2003 | Tenerz .......................... 600/585 |
| 2004/0167438 A1 | * | 8/2004 | Sharrow ....................... 600/585 |

* cited by examiner

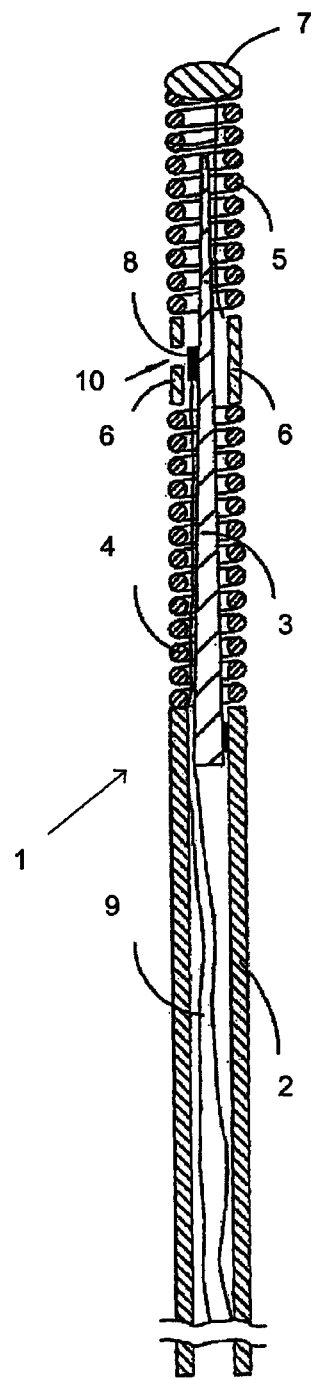
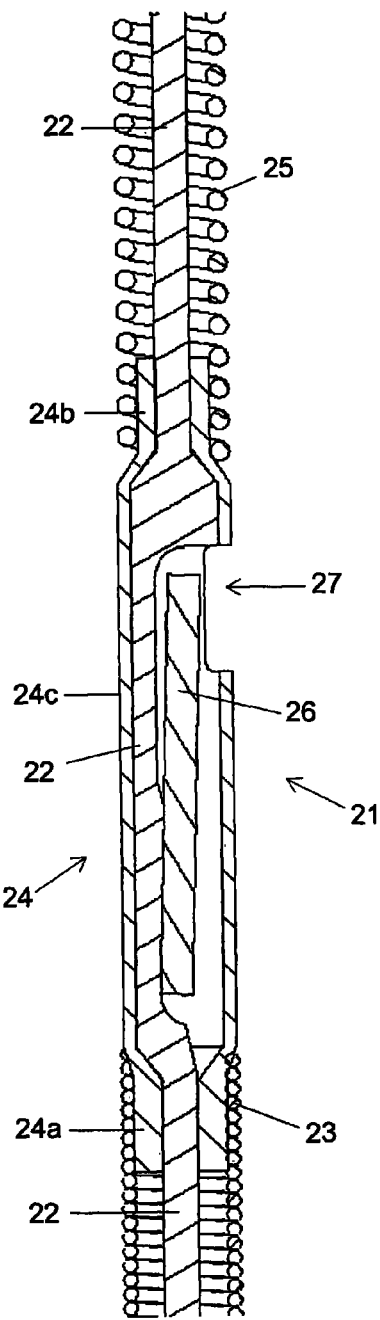
Fig. 1
(Prior Art)
Fig. 2

SENSOR AND GUIDE WIRE ASSEMBLY

FIELD OF THE INVENTION

The present invention relates generally to sensor and guide wire assemblies, in which a sensor element is mounted at the distal end of a guide wire for intravascular measurements of physiological variables in a living body, and particularly to the mounting arrangement of the sensor element, and more particularly to a jacket in which the sensor element is arranged.

BACKGROUND OF THE INVENTION

Sensor and guide wire assemblies in which a sensor is mounted at the distal end of a guide wire are known. In U.S. Pat. Re. 35,648, which is assigned to the present assignee, an example of such a sensor and guide wire assembly is disclosed, where a sensor guide comprises a sensor element, an electronic unit, a signal transmitting cable connecting the sensor element to the electronic unit, a flexible tube having the cable and the sensor element disposed therein, a solid metal wire, and a coil attached to the distal end of the solid wire. The sensor element comprises a pressure sensitive device, e.g. a membrane, with piezoresistive elements connected in a Wheatstone bridge-type of arrangement mounted thereon.

As is disclosed in, for example, U.S. Pat. No. 6,167,763, which also is assigned to the present assignee, the sensor element can be arranged inside a short tube (also referred to as a sleeve or jacket), which protects the sensor element and comprises an aperture through which the pressure sensitive device is in contact with the ambient medium. The U.S. Pat. No. 6,167,763 illustrates further that a first coil can be attached to the distal end of the jacket and that a similar second coil can be attached to the proximal end of the jacket. The solid metal wire—which in the art usually is referred to as the core wire—extends through the interior of the jacket and can be provided with an enlarged diameter portion adapted for mounting of the sensor element. The first and second coils are attached to the respective end of the jacket by gluing, or alternatively soldering. Glue or solder is also used to fixate the jacket to the core wire.

A principally different way of attaching a coil to a sleeve, which accommodates a sensor element, is disclosed in the U.S. Pat. No. 5,715,827 assigned to Cardiometrics, Inc. Here a portion of the outer mantle surface of the sleeve is provided with helical grooves in such a way that the coil can be screwed onto the sleeve. If needed, the coil can then be glued or soldered to the sleeve mantle. Although sensor and guide wire assemblies comprising a jacket designed according to the techniques presented herein in practise have proven to work very well, the design and attachment functionality of such a jacket can be improved, not least from a manufacturing point of view.

SUMMARY OF THE INVENTION

A sensor element of a sensor and guide wire assembly comprises an elongated, essentially rectangular chip with a pressure sensitive member in the form of a membrane made from polysilicon provided thereon. This sensor chip is arranged inside a jacket, which besides the sensor chip also accommodates a portion of a core wire and at least one electrical lead connected to the pressure sensitive member. A first coil is attached to the distal end of the jacket, and a second coil can be attached to the proximal end of the jacket. The first and second coils can be attached to the respective end of the jacket by gluing, or alternatively soldering. According to the prior art, the jacket has uniform inner and outer diameters over its entire length; and—for the purpose of the present invention—it should in particular be noted that these diameters are the same before and after the assembly of a sensor and guide wire assembly of which the jacket is a member.

It has now been realized that, because of the helical shapes of the coils, the contact area between an end surface of the jacket and an opposing end surface of the first or second coil is very small. A small contact area implies that the corresponding attachment area for a glue (or solder) provided between the jacket and the coil also is small, which consequently results in a joint whose strength is far from the maximum possible strength. Another problem is that it can be difficult to align and centre the jacket and the first and second coils with respect to each other, such that a smooth transition is provided between the end of a jacket and the opposing end of a coil.

It has further now been realized that a manufacturing step that involves the manual gluing of a jacket to a portion of a core wire is a relatively time consuming procedure; and the strength of the resulting joints will vary over time and will also differ from one operator to another. Similar disadvantages would also appear for a corresponding soldering procedure.

An object of the present invention is to remedy at least some of the problems encountered with a jacket according to the prior art. This object is accomplished by providing a jacket with at least one end portion having such mechanical properties that it can be crimped onto a core wire. By crimping an end portion of the jacket onto the core wire, a reliable attachment is achieved without the use of glue or solder. The outer diameter of the end portion after the crimping is preferably adapted to the inner diameter of a coil to be attached to the jacket. The coil can thereby be threaded onto the crimped end portion of the jacket, such that a large contact area between the coil and the jacket is provided. Preferably, the coil is then glued or soldered to the crimped end portion, and—as a result of the large attachment area—a very reliable joint has been accomplished.

A further advantage with the present jacket is that by adapting the outer diameter of the jacket after crimping to the inner diameter of a coil, the coil and the jacket are self-centred with respect to each other, something which both facilitates the manufacturing procedure and provides a sensor and guide wire assembly without any radially protruding step portions, which otherwise could arise from a mismatch between the jacket and an adjoining coil. To achieve a smooth outer surface of the sensor and guide wire assembly, the outer diameter of the middle portion of the jacket, which is not crimped, should be adapted to the outer diameters of the coils. After crimping of an end portion of a jacket, the surface of the jacket has thereby been provided with a circumferential edge, which provides a natural stop against which a coil can come to rest after having been threaded onto a crimped portion. Such a stop will further facilitate the manufacturing of a sensor and guide wire assembly.

The present invention is also directed to an improved method for producing a sensor and guide wire assembly including a jacket, in which a portion of a core wire is accommodated and to at least one end of which a coil is to be attached. According to an aspect of the invention, a manufacturing procedure comprises the steps of threading a jacket over a core wire, crimping a first end portion and then a second end portion of the jacket onto the core wire, threading a first coil over the first crimped end portion and then threading a second coil over the second crimped end portion, and gluing (or soldering or otherwise attaching) the first coil to the first end portion and then gluing (or soldering or otherwise attaching) the second coil to the second end portion.

BRIEF DESCRIPTION OF THE DRAWINGS

FIG. 1 illustrates schematically the general design of a sensor and guide wire assembly according to the prior art.

FIG. 2 illustrates schematically a portion of a sensor and guide wire assembly comprising a jacket according to the present invention.

DETAILED DESCRIPTION OF PREFERRED EMBODIMENTS OF THE INVENTION

Figure 3:
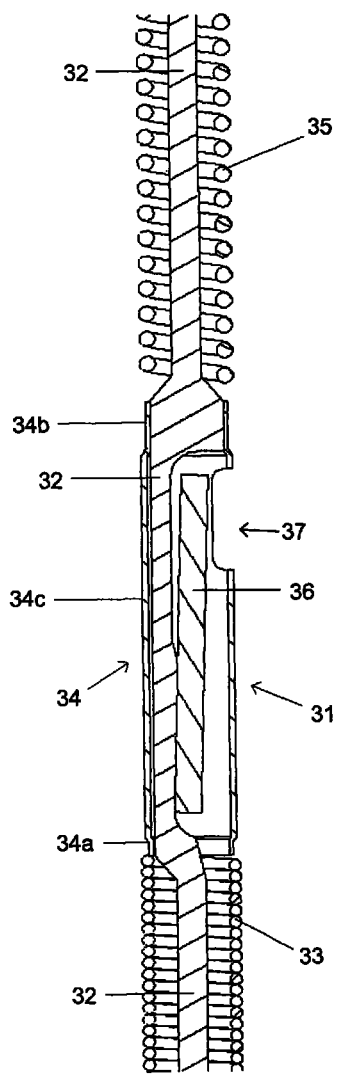
FIG. 3 illustrates a first alternative embodiment of a sensor and guide wire assembly comprising a jacket according to the present invention.

For better understanding of the context in which the present invention is going to be used, a sensor and guide wire assembly 1 of a conventional design is illustrated in FIG. 1. The sensor guide 1 comprises a hollow tube 2, a core wire 3, a first coil 4, a second coil 5, a jacket or sleeve 6, a dome-shaped tip 7, a sensor element or chip 8, and one or several electrical leads 9. The proximal end of the first coil 4 is attached to the distal end of the hollow tube 2, while the distal end of the first coil 4 is attached to the proximal end of the jacket 6. The proximal end of the second coil 5 is connected to the distal end of the jacket 6, and the dome-shaped tip 7 is attached to the distal end of the second coil 5. The core wire 3 is at least partly disposed inside the hollow tube 2 such that the distal portion of the core wire 3 extends out of the hollow tube 2 and into the second coil 5. The sensor element 8 is mounted on the core wire 3 at the position of the jacket 6, and is through the electrical leads 9 connected to an electronic unit (not shown in the figure). The sensor element 8 comprises a pressure sensitive device in the form of a membrane (not visible in the figure), which through an aperture 10 in the jacket 6 is in contact with a medium, such as blood, surrounding the distal portion of the sensor and guide wire assembly 1.

In FIG. 1 it should in particular be noted that the jacket 6 has a uniform tubular shape, and that the first and second coils 4, 5 only are in contact with a respective end of the jacket 6. Having in mind that a typical diameter for the sensor guide 1 is only 0.35 mm, it can be realized that the possible geometrical contact area between an end of the jacket and an end of an adjoining coil is very small. Furthermore, the actual contact area is even smaller. This is because of the helical shape of a coil, which implies that only a minor part of the coil end actually is in contact with a jacket end. Usually a coil is joined to a jacket end by means of glue, or alternatively solder; and the strength of the resulting joint is therefore far from the maximum possible strength.

The assembly of a sensor and guide wire assembly like the one shown in FIG. 1 is basically a manual procedure. It may therefore be appreciated that a coil having a tubular shape provides no means for facilitating the alignment of a coil to the jacket. After mounting, this means that there is a risk that there is gradual radial transition from a coil to the jacket; or, in other words, that the surface of the sensor guide is not completely smooth, which, of course, is highly unwanted.

A cross section of a portion of a sensor and guide wire assembly 21 according to the present invention is shown in FIG. 2. The sensor guide 21 comprises a core wire 22, a first or proximal coil 23, which is attached at the proximal end of a jacket or sleeve 24, the distal end of which is attached to a second or distal coil 25 and through which the core wire 22 extends. The sensor guide 21 comprises further a sensor element or chip 26, which is mounted to the core wire 22 at the position of the jacket 24 and is via one or several electrical leads (not shown in the figure) connected to an electronic unit (not shown in the figure). The sensor element 26 comprises a pressure sensitive device in the form of a membrane (not visible in the figure), which through an aperture 27 in the jacket 24 is in contact with a medium, such as blood, surrounding the illustrated portion of the sensor and guide wire assembly 21.

In contrast to the jacket 6 shown in FIG. 1, the jacket 24 shown in FIG. 2 is not uniform over its length, but comprises a first or proximal end portion 24a, a second or distal end portion 24b, and a middle portion 24c, such that the end portions 24a, b have reduced diameters in comparison with the middle portion 24c, whose outer diameter is essentially equal to the diameters of the first and second coils 23, 25. The first and second end portions 24a, b of the jacket 24 have been crimped onto the core wire 22; and the inner diameter of one end portion 24a (or 24b) is therefore equal to the diameter of the core wire 22 at this position. If the core wire 22 has a diameter that varies outside the middle portion 24c of the jacket 24, the first and second end portions 24a and 24b may have different inner diameters. By crimping an end portion of a jacket onto the core wire, a fast and reliable way of attaching a jacket to a core wire has been provided. Suitable pliers can be used for the crimping. For special designs of a sensor and guide wire assembly, only one end of a jacket could be crimped onto a core wire, while the other end is attached by means of conventional techniques, such as gluing or soldering.

As is illustrated in FIG. 2, after crimping, the diameter of the proximal end portion 24a of the jacket 24 is essentially equal to the inner diameter of the proximal coil 23, while the diameter of the distal end portion 24b is essentially equal to the inner diameter of the distal coil 25. During the assembly of the sensor guide 21, the proximal coil 23 is threaded over the proximal end portion 24a and the distal coil 25 is threaded over the distal end portion 24b. A crimped end portion of a jacket thereby acts as a guide portion, which facilitates the assembly of a sensor and guide wire assembly and ensures that a coil is aligned and centred with respect to the jacket. In comparison with sensor guides according to the prior art, the present invention provides a jacket whose crimped end portion provides a much larger contact area between a coil and the jacket, which, in turn, provides a much more reliable joint between these two elements. Here it should be emphasized that even if the outer diameter of a crimped end portion is not perfectly adapted to the inner diameter of an adjoining coil, the narrowing transition portion from a middle portion of a jacket to the crimped portion will anyway provide a contact area which is larger than the contact area provided when a coil is joined to the very end of a jacket (as is illustrated in FIG. 1). The requirement that an outer diameter of a crimped end portion is adapted to the inner diameter of an adjoining coil is therefore not crucial for practicing the present invention. Furthermore, if the outer diameter of a crimped end portion only is slightly smaller than the inner diameter of the adjoining coil, the fixation medium, e.g. glue or solder, will fill the remaining gap between these two elements.

As already may have been appreciated from the above, a method for assembling a sensor and guide wire assembly comprises the following steps: (a) arranging a jacket on a core wire and crimping a first end portion of the jacket onto the core wire, (a') crimping a second end portion of the jacket onto the core wire, (b) threading a portion of a first coil over the crimped first end portion of the jacket, (b') threading a portion of a second coil over the crimped second end portion of the jacket, (c) gluing (or alternatively soldering or otherwise joining) said portion of the first coil onto the crimped first end portion of the jacket, and (c') gluing (or alternatively soldering or otherwise joining) said portion of the second coil onto the crimped second end portion of the jacket. Optionally, steps (a'), (b') and (c') can be omitted without departing from the scope of the present invention.

In the embodiment disclosed in FIG. 2, the core wire 22 has an enlarged diameter at the position where the sensor chip 26 is mounted, i.e. the sensor chip 26 is mounted in a recess in the enlarged core wire portion. The proximal end portion 24a of the jacket 24 is crimped proximally of this enlarged core wire portion, while the distal end portion 24b is crimped distally of the enlarged core wire portion. In other words, the proximal and distal portions 24a, b have been crimped from a comparatively large diameter to a comparatively small diameter. An excessive crimping of a jacket can degrade the strength of the jacket, and to remedy this potential problem two alternative embodiments of the present invention are present in FIGS. 3 and 4, respectively.

In FIG. 3 a cross section of a portion of a sensor and guide wire assembly 31 according to the present invention is shown. The sensor guide 31 comprises a core wire 32, a first or proximal coil 33, which is attached at the proximal end of a jacket or sleeve 34, the distal end of which is attached to a second or distal coil 35 and through which the core wire 32 extends. The sensor guide 31 comprises further a sensor element or chip 36, which is mounted to the core wire 32 at the position of the jacket 34 and is through one or several electrical leads (not shown in the figure) connected to an electronic unit (not shown in the figure). The sensor element 36 comprises a pressure sensitive device in the form of a membrane (not visible in the figure), which through an aperture 37 in the jacket 34 is in contact with a medium, such as blood, surrounding the illustrated portion of the sensor and guide wire assembly 31. As in FIG. 2, the core wire 32 has an enlarged diameter at the position where the sensor element 36 is mounted. The jacket 34 comprises a first or proximal end portion 34a and a second or distal end portion 34b. In contrast to the first embodiment shown in FIG. 2, the first and second end portions 34a, b have been crimped onto the portion of the core wire 32 that has an enlarged diameter. By crimping the jacket 34 at the enlarged diameter portion of the core wire 32, the actual crimping of the jacket 34 is minimal and the accompanying strain on the material in the jacket 34 is consequently also reduced to a minimum. A possible disadvantage with this mounting technique is, however, that a crimped end portion 34a (or 34b) of the jacket 34 does not constitute a guide portion, over which a coil can be threaded and attached.

Figure 4:
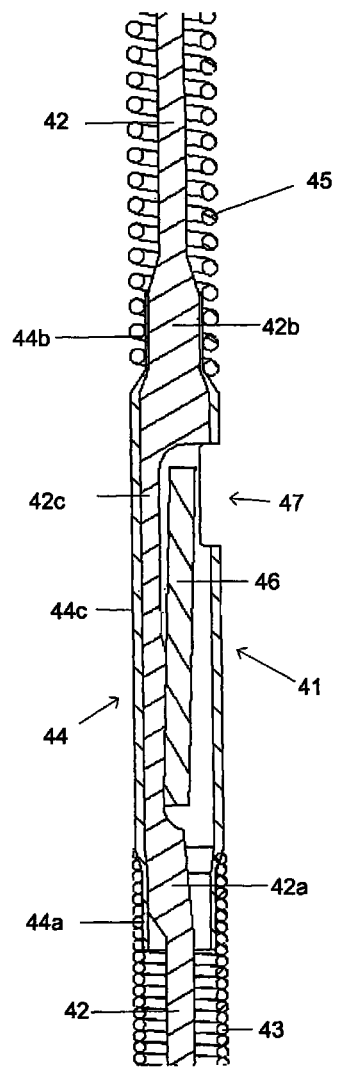
FIG. 4 illustrates a second alternative embodiment of a sensor and guide wire assembly comprising a jacket according to the present invention.

FIG. 4 shows a third embodiment of a sensor and guide wire assembly 41 according to the present invention. The sensor guide 41 comprises a core wire 42, a first or proximal coil 43, which is attached at the proximal end of a jacket or sleeve 44, the distal end of which is attached to a second or distal coil 45 and through which the core wire 42 extends.

The sensor guide 41 comprises further a sensor element or chip 46, which is mounted to the core wire 42 at the position of the jacket 44 and is through one or several electrical leads (not shown in the figure) connected to an electronic unit (not shown in the figure). The sensor element 46 comprises a pressure sensitive device in the form of a membrane (not visible in the figure), which through an aperture 47 in the jacket 44 is in contact with a medium, such as blood, surrounding the illustrated portion of the sensor and guide wire assembly 41. Like the previous embodiments shown in FIGS. 2 and 3, the sensor element 46 is mounted to a middle portion 42c of the core wire 42 where the core wire 42 has an enlarged diameter. As can be seen in FIG. 4 and in contrast to the previous embodiments, the core wire 42 comprises also a proximal portion 42a and distal portion 42b. These proximal and distal portions 42a, b have a respective diameter which is smaller than the diameter of the middle portion 42c but which is larger than the diameter of the rest of the core wire 42. The diameter of the proximal portion 42a may or may not be equal to the diameter of the distal portion 42b. The jacket 44 comprises a first or proximal end portion 44a and a second or distal end portion 44b. As can be seen in FIG. 4, the proximal end portion 44a has been crimped onto the proximal portion 42a of the core wire 42, and the distal end portion 44b has been crimped onto the distal portion 42b of the core wire 42. This third embodiment of the present invention may be regarded as a combination of the first and second embodiments described above in that the crimped proximal and distal end portions 44a, b of the jacket 44 act as guide portions over which a respective coil can be threaded and attached, but—due to the comparatively larger diameters of the proximal and distal portions 42a, b of the core wire 42 in comparison with corresponding portions of the core wires in the previous embodiments—the diameters of the proximal and distal end portions 44a, b of the jacket 44 are less reduced by the crimping.

The crimping technique according to the present invention may only be applied to one side of a jacket, i.e. the proximal (or distal) portion of the jacket can be crimped whereas the distal (or proximal) is left without crimping, or is attached to the core wire by conventional means, such as gluing or soldering. It is also conceivable to design a sensor and guide wire assembly in which two of the three embodiments presented above are combined, i.e. the proximal portion of the jacket is crimped according to one embodiment and the distal portion of the jacket is crimped according to one of the remaining two embodiments.

According to the present invention, a jacket adapted for crimping can have mantle thickness that varies over its length, e.g. the thickness of the mantle at a proximal or distal portion can be reduced in comparison with the mantle thickness in the middle portion. In particular, at least one portion of the material in the jacket can have a yield point that is lower than the yield point of the material in the core wire. Here, the portions of main interest are the jacket portions to be crimped and the core wire portions onto which the jacket portions are crimped, and jacket and core wire portions adjacent thereto. It should also be emphasized that the jacket can be crimped in different ways; it is in particular conceivable that jacket is not crimped uniformly around its periphery, but instead is only crimped at a portion of its circumference. A non-uniformly crimped jacket portion could, for example, have a cross-section in the shape of the letter D. Even more localized crimping techniques are conceivable. When a jacket is crimped in such a non-uniform way, a core wire can assume an off-centre position inside the jacket.

Although the present invention has been described with reference to specific embodiments, also shown in the appended drawings, it will be apparent for those skilled in the art that many variations and modifications can be done within the scope of the invention as described in the specification and defined with reference to the claims below. It should in particular be noted that the improved characteristics of a sensor guide provided with a jacket according to the invention are not dependent on the design of the other parts of the sensor guide. For example, the core wire, to which the jacket is attached, may extend along essentially all the length of the sensor guide, or the core wire may only be provided at the distal portion of the sensor guide.

The invention claimed is:

1. A sensor and guide wire assembly for intravascular measurement of at least one physiological variable in a living body, comprising:
a core wire having an enlarged sensor portion at which a sensor chip is disposed, and a tip portion located distal of the enlarged sensor portion, a diameter of the enlarged sensor portion being greater than a diameter of the tip portion;
a first coil; and
a jacket surrounding at least part of the enlarged sensor portion of the core wire and accommodating at least a portion of the sensor chip, the jacket having a circumferential wall with an opening extending therethrough to allow fluid to enter the jacket and contact the sensor chip,
wherein a distal portion of the jacket, including a distal-most end of the jacket, is crimped onto the core wire, such that a diameter of the distal-most end of the jacket is smaller than a diameter of a central portion of the jacket, and
wherein a proximal portion of the first coil is attached to the crimped distal portion of the jacket.

2. The sensor and guide wire assembly according to claim 1, wherein material in the distal portion of the jacket has a lower yield point than material in the core wire at a portion onto which the distal portion of the jacket is crimped.

3. The sensor and guide wire assembly according to claim 1, further comprising:
a second coil,
wherein a proximal portion of the jacket, including a proximal-most end of the jacket, is crimped onto the core wire, such that a diameter of a proximal-most end of the jacket is smaller than the diameter of the central portion of the jacket, and
wherein a distal portion of the second coil is attached to the crimped proximal portion of the jacket.

4. The sensor and guide wire assembly according to claim 3, wherein material in the proximal portion of the jacket has a lower yield point than material in the core wire at a portion onto which the proximal portion of the jacket is crimped.

5. The sensor and guide wire assembly according to claim 1, wherein the crimped distal portion of the jacket has an outer diameter that is substantially equal to an inner diameter of the first coil.

6. The sensor and guide wire assembly according to claim 3, wherein the crimped proximal portion of the jacket has an outer diameter that is substantially equal to an inner diameter of the second coil.

7. A sensor and guide wire assembly according to claim 1, wherein the core wire does not comprise the jacket such that the core wire and the jacket are separate pieces.

8. The sensor and guide wire assembly according to claim 1, wherein the distal portion of the jacket, including the distal-most end of the jacket, is crimped onto the tip portion of the core wire, distal of the enlarged sensor portion.

9. A method for manufacturing a sensor and guide wire assembly for intravascular measurement of at least one physiological variable in a living body, the method comprising:
providing a core wire that includes an enlarged sensor portion at which a sensor chip is disposed, and a tip portion located distal of the enlarged sensor portion, a diameter of the enlarged sensor portion being greater than a diameter of the tip portion;
arranging a jacket on a portion of the core wire such that the jacket surrounds at least part of the enlarged sensor portion of the core wire, the jacket having a circumferential wall with an opening extending therethrough to allow fluid to enter the jacket and contact the sensor chip;
crimping a distal portion of the jacket, including a distal-most end of the jacket, onto the core wire, such that a diameter of the distal-most end of the jacket is smaller than a diameter of a central portion of the jacket; and
attaching a proximal portion of a first coil to the crimped distal portion of the jacket.

10. The method according to claim 9, further comprising the steps of:
crimping a proximal portion of the jacket, including a proximal-most end of the jacket, onto the core wire, such that a diameter of a proximal-most end of the jacket is smaller than a diameter of a central portion of the jacket; and
attaching a distal portion of a second coil to the crimped proximal portion of the jacket.

11. The method according to claim 9, wherein the distal portion of the jacket, including the distal-most end of the jacket, is crimped onto the tip portion of the core wire, distal of the enlarged sensor portion.

12. A sensor and guide wire assembly for intravascular measurement of at least one physiological variable in a living body, comprising:
a core wire having an enlarged sensor portion at which a sensor chip is disposed, and a tip portion located distal of the enlarged sensor portion, a diameter of the enlarged sensor portion being greater than a diameter of the tip portion;
a first coil;
a second coil; and
a jacket surrounding at least part of the enlarged sensor portion of the core wire and accommodating at least a portion of the sensor chip, the jacket having a circumferential wall with an opening extending therethrough to allow fluid to enter the jacket and contact the sensor chip,
wherein a distal portion of the jacket, including a distal-most end of the jacket, is crimped onto the core wire, such that a diameter of a distal-most end of the jacket is smaller than a diameter of a central portion of the jacket,
wherein a proximal portion of the jacket, including a proximal-most end of the jacket, is crimped onto the core wire, such that a diameter of a proximal-most end of the jacket is smaller than the diameter of the central portion of the jacket, wherein a proximal portion of the first coil is attached to the crimped distal portion of the jacket, wherein a distal portion of the second coil is attached to the crimped proximal portion of the jacket, wherein the crimped distal portion of the jacket has an outer diameter that is substantially equal to an inner diameter of the first coil, and wherein the crimped proximal portion of the jacket has an outer diameter that is substantially equal to an inner diameter of the second coil.

13. The sensor and guide wire assembly according to claim 12, wherein the distal portion of the jacket, including the distal-most end of the jacket, is crimped onto the tip portion of the core wire, distal of the enlarged sensor portion.

* * * * *